United States Patent
Oleen

(10) Patent No.: US 8,564,436 B2
(45) Date of Patent: *Oct. 22, 2013

(54) WALLET

(76) Inventor: Victoria A. Oleen, Napa, CA (US)

(*) Notice: Subject to any disclaimer, the term of this patent is extended or adjusted under 35 U.S.C. 154(b) by 419 days.

This patent is subject to a terminal disclaimer.

(21) Appl. No.: 12/948,153

(22) Filed: Nov. 17, 2010

(65) Prior Publication Data

US 2011/0215026 A1 Sep. 8, 2011

Related U.S. Application Data

(63) Continuation-in-part of application No. 12/717,215, filed on Mar. 4, 2010, now Pat. No. 8,400,300.

(51) Int. Cl.
*G08B 13/08* (2006.01)

(52) U.S. Cl.
USPC ..... 340/545.6; 206/581; 220/521; 340/691.5; 340/693.5; 340/815.4

(58) Field of Classification Search
USPC .......... 340/545.6, 545.2, 545.3, 568.1, 568.7, 340/691.1, 691.2, 691.5, 692, 693.5, 815.4, 340/815.65, 384.3, 384.7; 206/581; 220/521; 150/112, 113
See application file for complete search history.

(56) References Cited

U.S. PATENT DOCUMENTS

| | | | | |
|---|---|---|---|---|
| 4,574,822 A * | 3/1986 | Helinsky | ........................ | 132/286 |
| 4,961,522 A * | 10/1990 | Weber | ........................... | 224/585 |
| 5,638,957 A * | 6/1997 | Brasier | ........................ | 206/581 |
| 5,926,099 A * | 7/1999 | Unum | ........................ | 340/686.1 |
| 6,168,022 B1 * | 1/2001 | Ward et al. | ..................... | 206/581 |
| 6,412,652 B1 * | 7/2002 | Woram et al. | .................. | 220/521 |
| 6,540,084 B2 * | 4/2003 | Silvers | .......................... | 206/581 |
| 7,284,790 B1 * | 10/2007 | Brewer | ..................... | 297/184.13 |
| 7,367,449 B2 * | 5/2008 | Kaminski et al. | ............. | 206/6.1 |
| 7,942,296 B1 * | 5/2011 | Johnson | ........................ | 224/578 |
| 2006/0289582 A1 * | 12/2006 | Killilea | ........................ | 224/577 |
| 2007/0122066 A1 * | 5/2007 | Landay | ........................... | 383/16 |
| 2007/0151895 A1 * | 7/2007 | Patterson | ...................... | 206/581 |
| 2012/0043358 A1 * | 2/2012 | Kelly | ......................... | 224/148.2 |

* cited by examiner

*Primary Examiner* — Thomas Mullen
(74) *Attorney, Agent, or Firm* — Dale J. Ream

(57) ABSTRACT

A wallet includes semi-rigid first and second portions each having outer and inner sides, the second portion being hingedly coupled to the first portion whereby the second portion is movable relative to the first portion to define open and closed configurations. The first portion inner side includes a pocket. A foldable changing pad is operatively coupled to at least one of the first portion and the second portion. A flexible container is positioned proximate one of the first portion and the second portion, the container having a bottom and at least one wall extending upwardly from the bottom that are movable between collapsed and expanded configurations defining a reservoir for holding a liquid therein, the at least one wall defining an outlet. A lid is removably coupled to the container outlet. A liquid delivery member is coupled to the lid for selectively transferring the liquid through the lid.

19 Claims, 7 Drawing Sheets

WALLET

CROSS-REFERENCE TO RELATED APPLICATIONS

The present application is a continuation-in-part of U.S. patent application Ser. No. 12/717,215, filed Mar. 4, 2010, now issued as U.S. Pat. No. 8,400,300 and titled "Wallet", which is incorporated herein by reference.

BACKGROUND OF THE INVENTION

This invention relates generally to infant accessory items and, more particularly to a diaper changing wallet having structures that enable an array of products useful for changing an infant's diaper to be removably secured as well as entertaining an infant during a diaper changing procedure.

Changing the diaper of an infant, especially when away from home, may be challenging in that a flat, clean environment, a host of cleaning supplies, and a fresh diaper must all be brought together for use. The myriad of needed items, such as cleaning wipes, creams, powder, medicine, diaper, and a changing pad are traditionally carried in a baby bag which may be overly bulky when traveling away from home.

Various devices have been proposed in the art for holding diaper changing accessories in a manner more convenient and portable than a traditional baby bag. Although assumably effective for their intended purposes, the existing devices do not provide a stylish compact wallet capable of being carried by a man or woman apart from a baby bag and which also includes audible and visual attractions to maintain the attention of a baby during a diaper changing event.

Therefore, it would be desirable to have a diaper changing wallet that holds baby changing items in a stylish, compact wallet apart from a traditional baby bag. Further, it would be desirable to have a diaper changing wallet that includes audio and visual attractions to keep a baby's attention. In addition, it would be desirable to have a diaper changing wallet that includes a collapsible baby bottle that may be expanded when filled with water.

SUMMARY OF THE INVENTION

A wallet according to the present invention includes semi-rigid first and second portions each having an outer side and an inner side, the second portion being hingedly coupled to the first portion whereby the second portion is movable relative to the first portion to define open and closed configurations. The first portion inner side includes a pocket. A foldable changing pad is operatively coupled to at least one of the first portion and the second portion. A flexible container is positioned proximate one of the first portion and the second portion, the container having a bottom and at least one wall extending upwardly from the bottom that are movable between a collapsed configuration and an expanded configuration defining a reservoir for holding a liquid therein, the at least one wall defining an outlet. A lid is removably coupled to the container outlet. A liquid delivery member is coupled to the lid for selectively transferring the liquid through the lid.

Therefore, a general object of this invention is to provide a wallet that in which one or more diapers and wipes may be positioned in an opposing pocket and compartment.

Another object of this invention is to provide in a wallet, as aforesaid, a foldable changing pad removably situated so as to isolate the pocket of diapers from the wipes.

Still another object of this invention is to provide a wallet, as aforesaid, that provides audio and video components that may be selected using user input buttons.

Yet another object of this invention is to provide a wallet, as aforesaid, that includes sensors in communication with a processor for activating and deactivating the audio and visual components.

A particular object of this invention is to provide a wallet, as aforesaid, that includes a collapsible bottle that takes up very little space when collapsed and that may be expanded when filled with water such as when mixing formula for feeding a baby.

A further object of this invention is to provide a wallet, as aforesaid, that is easy and stylish to carry and cost-effective to manufacture.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

Figure 1:
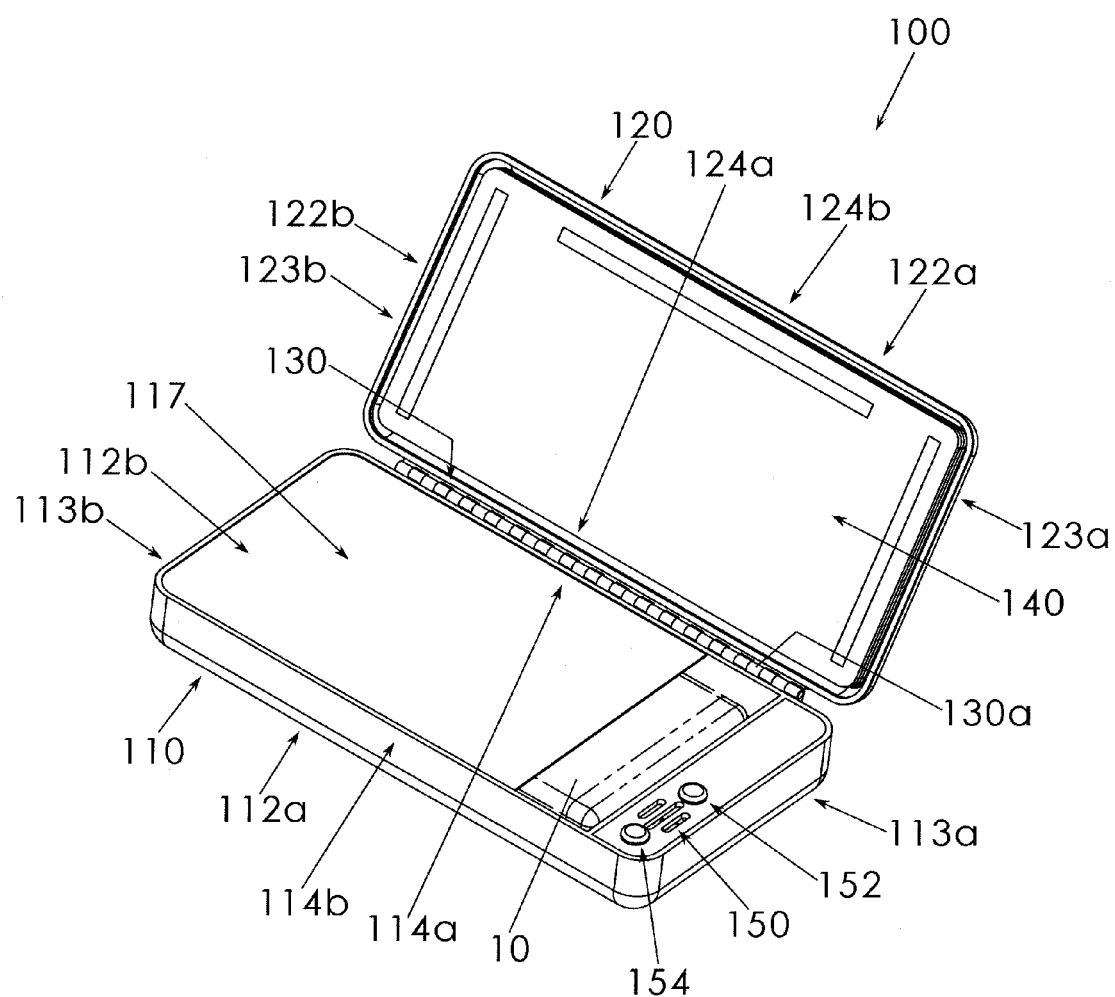
FIG. 1 is a perspective view of a wallet according to a preferred embodiment of the present invention in an open configuration.

Wallets according to the present invention will now be described in detail with reference to FIGS. 1 through 7 of the accompanying drawings. More particularly, a wallet 100 for carrying baby supplies according to one embodiment includes semi-rigid first and second portions 110, 120.

As shown in FIGS. 1 through 4, the first portion 110 has an outer side 112a and an inner side 112b, upper and lower ends 113a, 113b, and opposed sides 114a, 114b. The second portion 120 has an outer side 122a and an inner side 122b, upper and lower ends 123a, 123b, and opposed sides 124a, 124b. The first and second portions 110, 120 are hingedly coupled together (e.g., at sides 114a, 124a by hinge 130) such that the second portion 120 is movable relative to the first portion 110 to define open and closed configurations. When at the closed configuration, the first and second portions 110, 120 may enclose an interior space. FIGS. 1 through 4 all show the first and second portions 110, 120 at the open configuration, and those skilled in the art will understand the closed configuration without additional figures. Means for temporarily maintaining the first and second portions 110, 120 at the closed configuration, such as a spring-loaded hinge 130a, a latch, a strap, or any other acceptable element, may be included.

Figure 2:
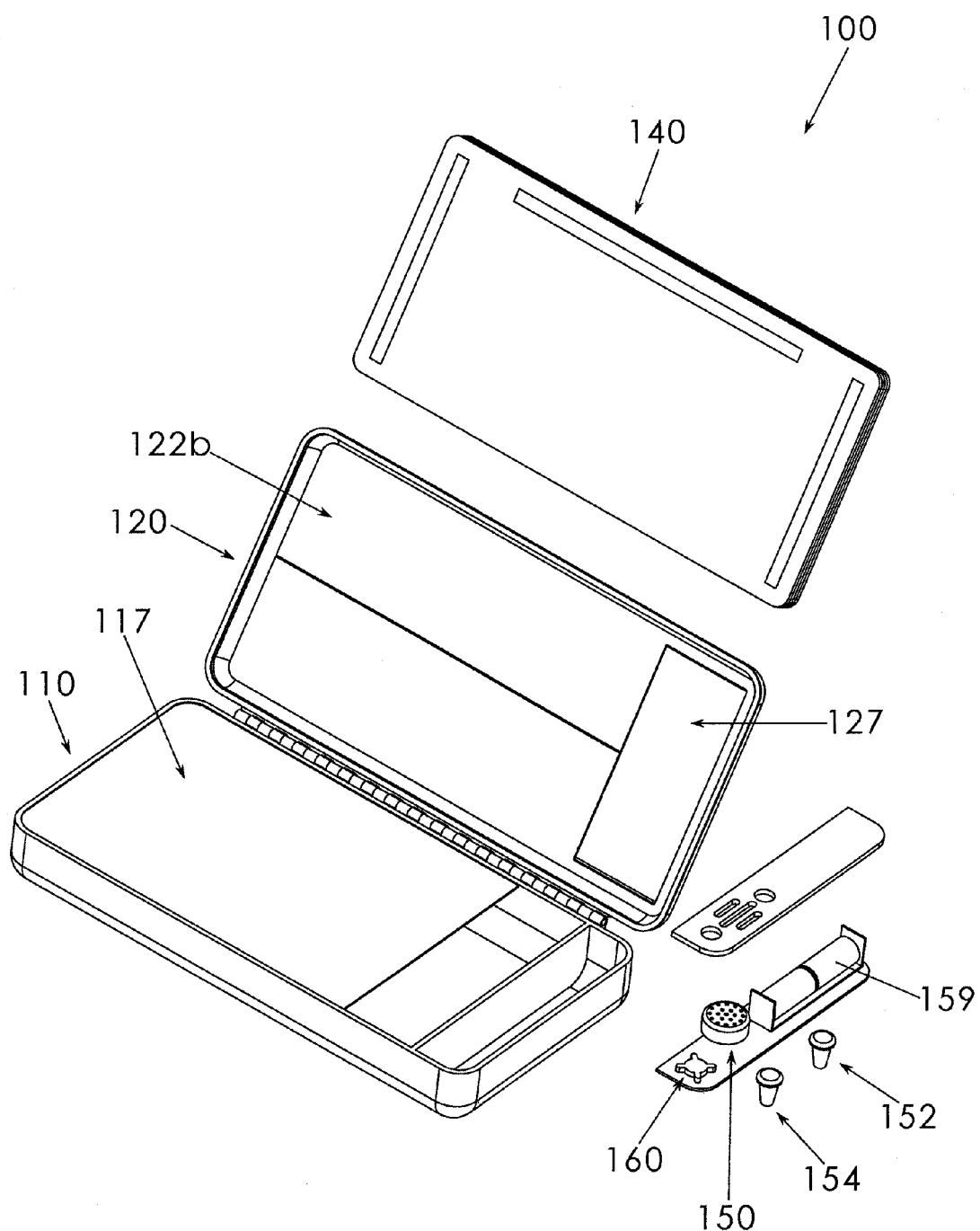
FIG. 2 is an exploded view of the wallet as in FIG. 1.

FIGS. 1 through 4 further show a pocket 117 at the first portion inner side 112b for holding a diaper 10. The pocket 117 may extend continuously from the first portion lower end 113b to a position closer to the first position upper end 113a than to the first portion lower end 113b, as shown. Alternately, the pocket 117 may include a band extending between the sides 114a, 114b (but that does not extend to the first portion lower end 113b). Turning now to FIG. 2, a compartment 127 may be at the second portion inner side 122b for holding a moist wipe or other item. The compartment 127 may be isolated from the pocket 117, such as by a cover, partition, or other element.

Figure 3:
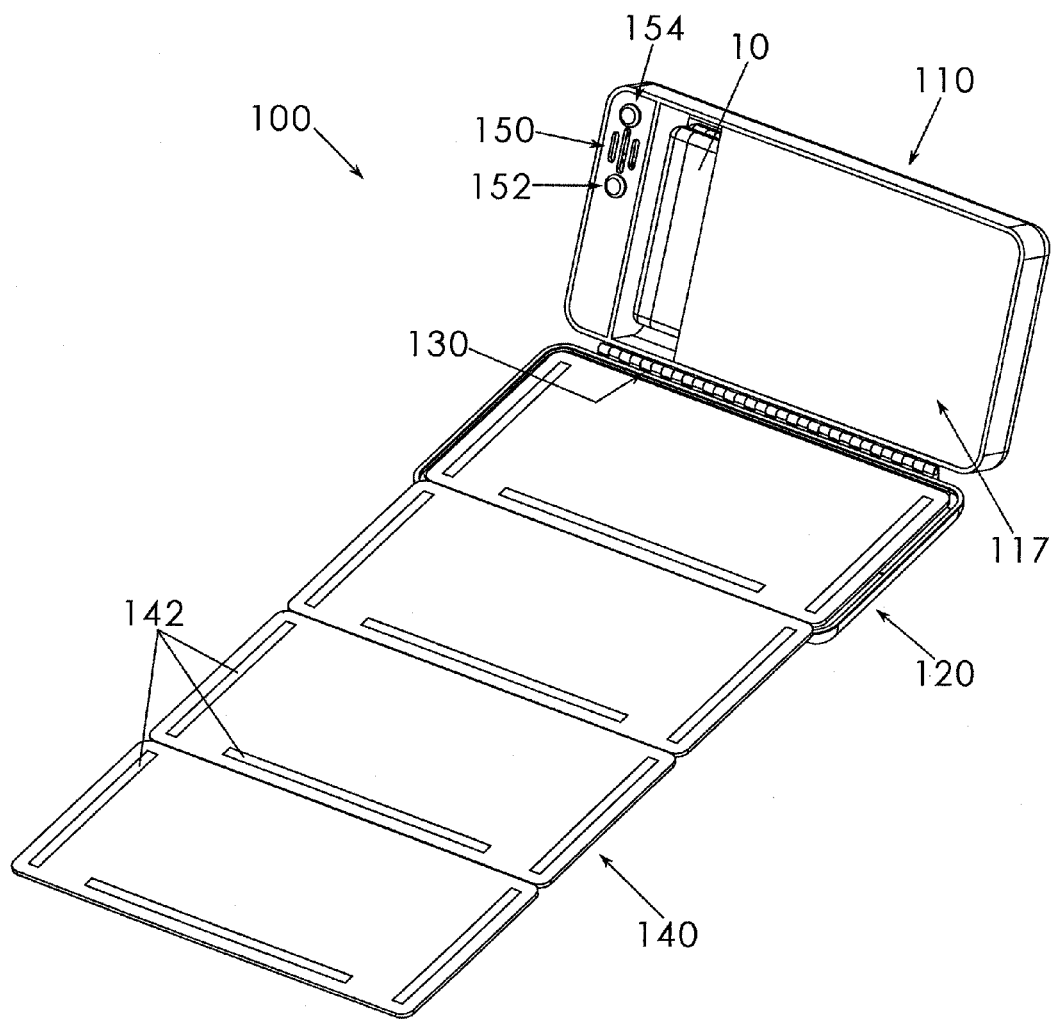
FIG. 3 is a perspective view of the wallet as in FIG. 1 from another angle and with a foldable changing pad in an extended configuration.
Figure 4:
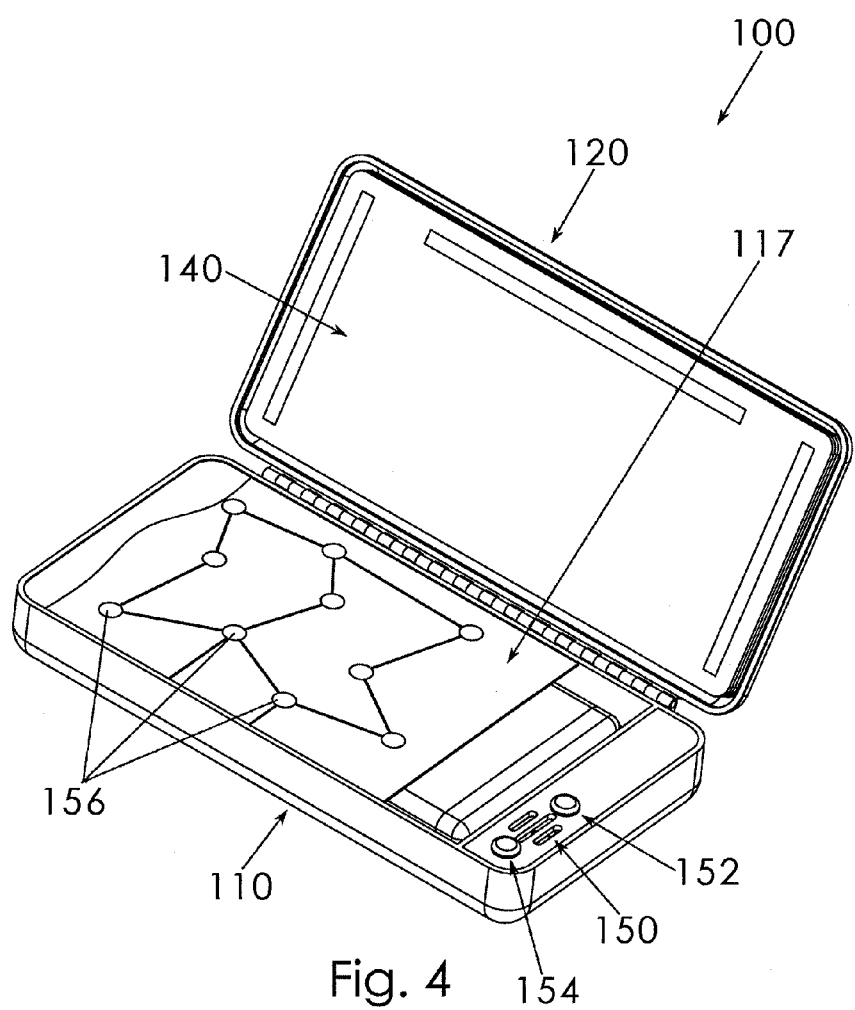
FIG. 4 is another perspective view of the wallet as in FIG. 1 revealing a plurality of lights.
Figure 5:
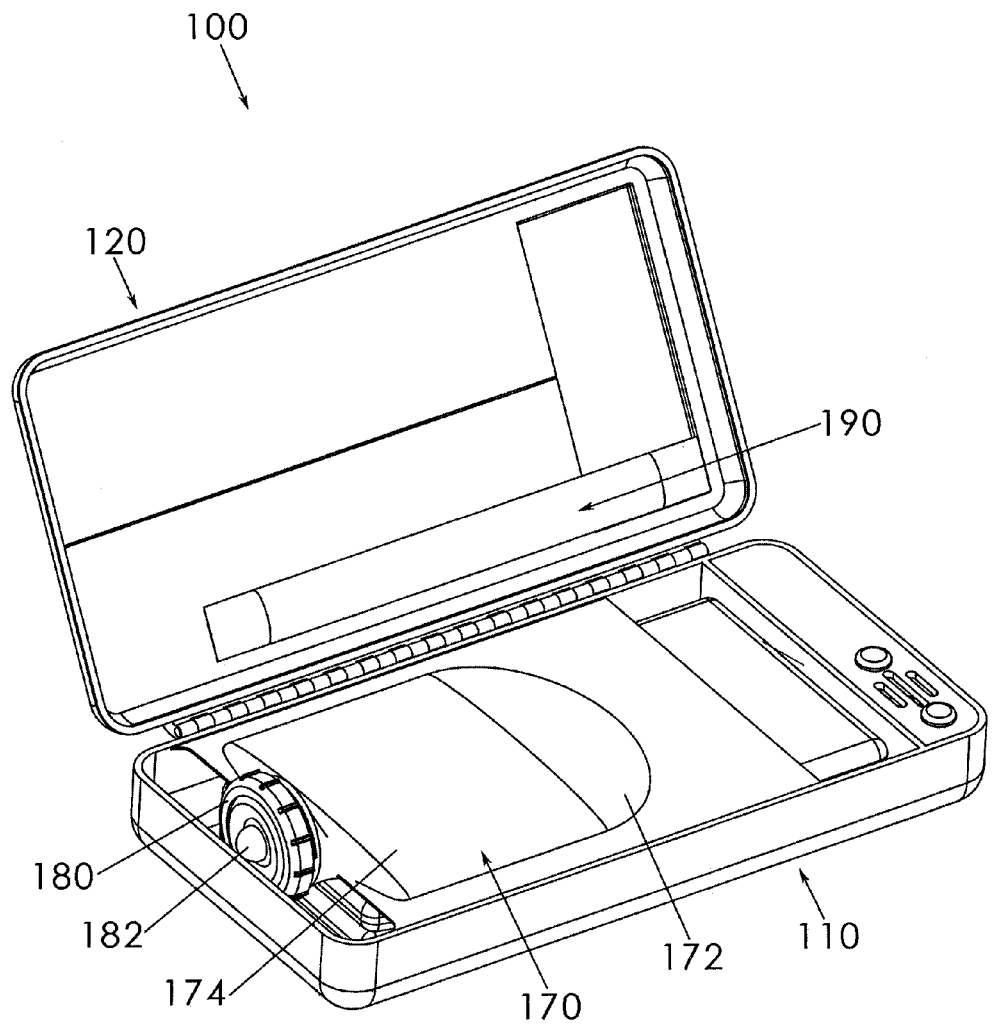
FIG. 5 is a perspective view of the wallet as in FIG. 1 including a collapsible bottle and food packet.

A folding changing pad 140 may be operatively coupled to the first portion 110 and/or the second portion 120. As shown in FIGS. 1, 3, and 4, the changing pad 140 may be located such that it is in the interior space. In such a configuration, the changing pad 140 may isolate the pocket 117 from the compartment 127. The changing pad 140 may include at least one magnet 142 (FIG. 3) for temporarily attaching the changing pad 140 to a ferrous or ferric surface. Alternately, the changing pad 140 may be removably positioned within another pocket (an "auxiliary" pocket) on the exterior of the wallet 100 (not shown). The auxiliary pocket may also include a plurality of slots for holding credit cards and the like such that wallet 100 may be used for both baby supplies and traditional wallet functions.

A speaker 150 and means for determining when the first and second portions 110, 120 are at the open configuration (e.g., push button 152, pressure sensor, light sensor, etc.) may be included, as shown throughout the drawings, and a processor 160 (FIG. 2) may be in data communication with both. A user input 154 (e.g., at least one button, switch, etc.) and/or at least one light 156 (FIG. 4) may also be in data communication with the processor 160, and at least one battery 159 (FIG. 2) or other power supply may power the electrical components. If a plurality of lights 156 are included, the lights 156 may emit different colors such that at least one light 156 outputs a color different from a color of at least one other light 156.

Various programming, including that described herein, for example, may be included. More particularly, programming may be included to cause the processor 160 to automatically actuate the speaker 150 an amount of time after the push button 152 determines that the first and second portions 110, 120 are at the open configuration, and programming may be included to cause the processor 160 to automatically actuate the light(s) 156 an amount of time after the push button 152 determines that the first and second portions 110, 120 are at the open configuration. The speaker 150 and light(s) 156 may be actuated generally simultaneously, or the amount of delay may differ. Programming may select the amount of time for the delay(s) based on data from the user input 154.

Especially if a plurality of lights 156 are included, the lights 156 may be actuated in one or more patterns. Programming may select the pattern based on data from the user input 154, and programming may further select between data to output through the speaker 150 based on data from the user input 154. Moreover, programming may cause the processor 160 to automatically deactivate the speaker 150 and light(s) 156 when the push button 152 determines that the first and second portions 110, 120 have moved to the closed configuration.

Figure 6A:
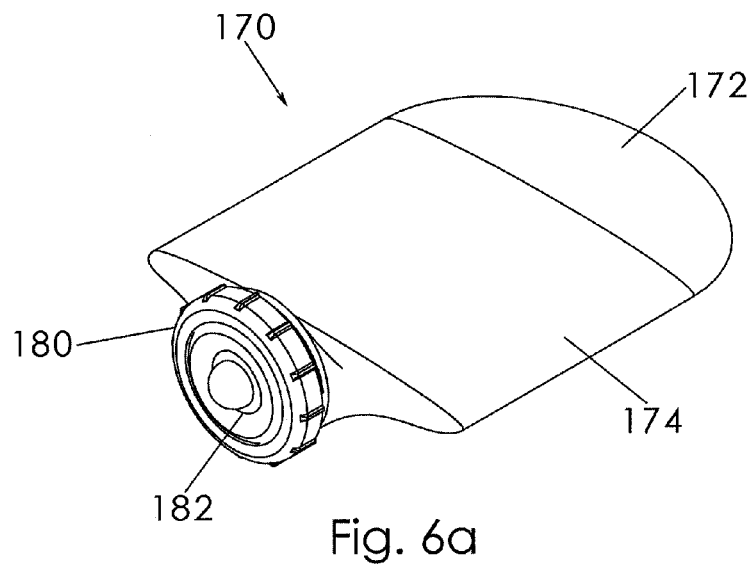
FIG. 6a is a perspective view of the flexible container removed from the wallet illustrated in a collapsed configuration.
Figure 6B:
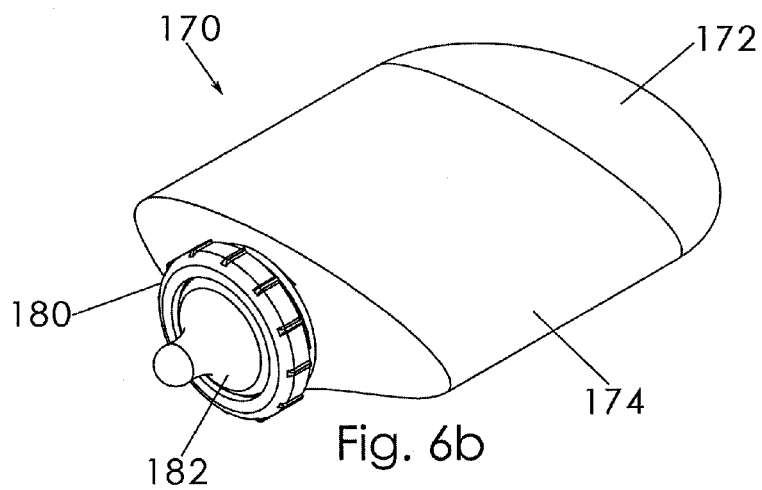
FIG. 6b is another perspective view of the flexible container removed from the wallet illustrated in an expanded configuration.

In another aspect of the diaper wallet 100, a flexible container 170 is positioned proximate one of either the first portion 110 or the second portion 120 of the wallet 100. The flexible container 170 includes a bottom 172 and at least one side wall 174 extending upwardly therefrom so as to define an outlet 176 at an upper end thereof. It is understood that a container 170 having only a single wall 174 is a bottle having a cylindrical configuration. The side wall 174 may include a neck between upper ends of the side wall 174 and the outlet 176. Preferably, the flexible container 170 is constructed of a thin plastic material that is foldable although materials such as rubber or the like may also be suitable. The flexible container 170 is movable between a collapsed or generally flattened configuration (FIG. 6a) and an expanded configuration (FIG. 6b). At the expanded configuration, the bottom 172 and at least one side wall 174 of the flexible container 170 defines a reservoir capable of holding water or other liquid in a watertight manner. In fact, the flexible container 170 moves/expands from the collapsed configuration to the expanded configuration when a liquid is inserted therein. Stated another way, the flexible container 170 is at the collapsed configuration when no liquid is in the reservoir but is in the expanded configuration when a liquid is received therein. The material of the bottom 172 and upstanding wall 174 is liquid impermeable such that liquid received therein does not leak.

It should be appreciated, however, that the container 170 may alternatively be constructed of a generally rigid material that is not collapsible. If a substantially rigid construction is employed, it is understood that a generally thin configuration is preferred so that the container 170 may be positioned within the wallet 100 without substantially increasing the thickness thereof. In other words, a generally flat, oval, or elongate construction having a thin thickness is preferred.

Figure 7:
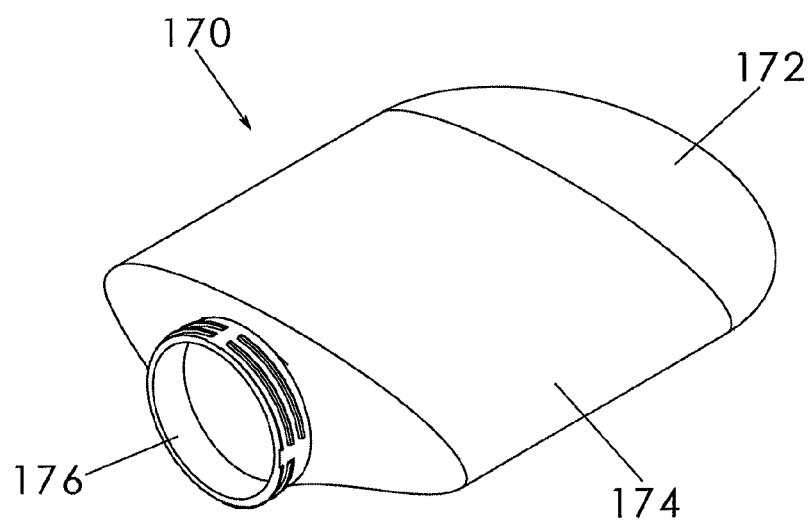
FIG. 7 is a perspective view of the flexible container as in FIG. 6b with the lid removed from the container.

A lid 180 is removably coupled to an upper edge of the at least one wall 174 for sealing or unsealing the outlet 176, respectively (FIG. 7). In other words, a liquid may be poured into the container 170 when the lid 180 is removed from the outlet 176 and prevented from being removed therefrom when the lid 180 covers the outlet 176. The lid 180 may be coupled to the upper edge of the upstanding wall 174 with threads complementary to threads on the upper edge or any other suitable fastening or sealing means (FIG. 7).

A liquid delivery member 182 may be coupled to the lid 180 for selectively transferring liquid from the container 170 through the outlet 176 and lid 180. Preferably, the flexible container 170 is a baby bottle, the lid 180 is threadably coupled thereto and defines a central opening, and the delivery member 182 is a plastic or rubber nipple that is received in the central opening although the lid 180 and delivery member 182 may be integrated as a pour spout, a pop-up spout, or other delivery means.

A packet 190 may also be positioned proximate one of either the first portion 110 or the second portion 120 of the wallet 100. The packet 190 may be constructed of paper or cardboard and have the configuration substantially similar to that of a disposable envelope although a plastic construction for repeated use would also work. More particularly, the packet 190 may include a closed bottom and elongate side walls defining an open top and a cover member selectively covering the open top. The packet 190 defines an interior space capable of containing a powdered food stuff, such as dry baby formula.

In use, one or more diapers 10 may be placed in the pocket 117 and one or more moist wipes may be placed in the compartment 127. The delay(s), data to be output through the speaker 150, and light pattern may be selected using the user input 154. When the first and second portions 110, 120 are moved from the closed configuration to the open configuration, the push button 152 may detect the transition and the processor 160 may automatically actuate the speaker 150 and/or the light(s) 156 after the selected delay. The changing pad 140 may be used as a sanitary changing surface, and the speaker 150 and/or light(s) 156 may distract and occupy a child while its diaper is changed. When the first and second portions 110, 120 are moved to the closed configuration, the push button 152 may detect the transition and the processor 160 may automatically deactivate the speaker 150 and/or the light(s) 156.

In addition, the collapsible bottle 170 (referred to above as the flexible container) may be prepared to feed a baby. More particularly, the collapsible bottle 170 may be removed from the wallet 100 and the lid 180 may be removed. Then, a desired portion of powdered baby formula may be dumped from the packet 190 (or the entire volume of the packet) into the bottle 170 through the now uncovered outlet 176 along with an appropriate amount of water. As described above, insertion of water into the bottle/container will cause the container 170 to expand to the expanded configuration.

When the lid 180 is engaged to cover the outlet 176, the container 170 may be shaken to dissolve the baby formula in the water and a baby may be fed in a traditional manner. When finished, the container 170 may be flattened to the collapsed configuration and again stored in the wallet 100.

It is understood that while certain forms of this invention have been illustrated and described, it is not limited thereto except insofar as such limitations are included in the following claims and allowable functional equivalents thereof.

The invention claimed is:

1. A wallet, comprising:
a semi-rigid first portion having an outer side and an inner side;
a semi-rigid second portion having an outer side and an inner side, said second portion being hingedly coupled to said first portion whereby said second portion is movable relative to said first portion between a closed configuration in which said inner side of said second portion and said inner side of said first portion face each other in an generally adjacent relationship and an open configuration in which said inner side of said second portion is offset from and displaced from said inner side of said first portion;
means for temporarily maintaining said first and second portions at said closed configuration;
a pocket at said first portion inner side for holding a diaper;
a folding changing pad operatively coupled to at least one of said first portion and said second portion;
a container operatively positioned proximate one of said first portion and said second portion, said container having a bottom and at least one wall extending upwardly from said bottom that collectively define a reservoir so as to selectively hold a liquid therein, said at least one wall defining an outlet;
a lid removably coupled to said container outlet; and
a liquid delivery member coupled to said lid for selectively transferring said liquid through said lid.

2. The wallet as in claim 1, wherein:
said container is a flexible container, said bottom and said at least one wall being movable between a collapsed configuration and an expanded configuration;
a liquid is selectively receivable through said container outlet when said lid is removed from said outlet;
said container is at said collapsed configuration when said reservoir does not include said liquid; and
said container is at said expanded configuration when said reservoir includes said liquid.

3. The wallet as in claim 2, further comprising:
a packet removably positioned in one of said first and second portion that defines an interior space and at least one selectively open end.

4. The wallet of claim 3, further comprising:
a speaker;
means for determining when said first and second portions are at said open configuration;
a processor in data communication with said speaker and said means for determining; and
wherein said processor is programmed to automatically actuate said speaker an amount of time after said means for determining determines that said first and second portions are at said open configuration.

5. The wallet as in claim 2, further comprising:
a speaker;
means for determining when said first and second portions are at said open configuration;
a processor in data communication with said speaker and said means for determining; and
wherein said processor is programmed to automatically actuate said speaker an amount of time after said means for determining determines that said first and second portions are at said open configuration.

6. The wallet of claim 5, further comprising:
a light in data communication with said processor; and
wherein said processor is programmed to automatically actuate said light an amount of time after said means for determining determines that said first and second portions are at said open configuration.

7. The wallet of claim 5, further comprising:
a plurality of lights in data communication with said processor; and
wherein said processor is programmed to automatically actuate said plurality of lights in a pattern an amount of time after said means for determining determines that said first and second portions are at said open configuration.

8. The wallet of claim 7, wherein at least one said light outputs a color different from a color of at least one other said light.

9. The wallet of claim 5, further comprising:
a user input in data communication with said processor; and
wherein said processor is programmed to select said amount of time based on data from said user input.

10. The wallet of claim 5, further comprising:
a user input in data communication with said processor; and
wherein said processor is programmed to select between data to output through said speaker based on data from said user input.

11. The wallet of claim 5, further comprising wherein said processor is programmed to automatically deactivate said speaker when said means for determining determines that said first and second portions have moved to said closed configuration.

12. The wallet of claim 11, further comprising:
a plurality of lights in data communication with said processor;
wherein said processor is programmed to automatically actuate said plurality of lights in a pattern an amount of time after said means for determining determines that said first and second portions are at said open configuration; and
wherein said processor is programmed to automatically deactivate said plurality of lights when said means for determining determines that said first and second portions have moved to said closed configuration.

13. The wallet of claim 12, wherein at least one said light outputs a color different from a color of at least one other said light.

14. The wallet of claim 13, further comprising:
a user input in data communication with said processor; and
wherein said processor is programmed to select between data to output through said speaker based on data from said user input.

15. The wallet of claim 1, wherein:
said first portion has upper and lower ends; and
said pocket extends continuously from said first portion lower end to a position closer to said first portion upper end than to said first portion lower end.

16. The wallet of claim 1, further comprising a compartment at said second portion inner side for holding a moist wipe, said compartment being isolated from said pocket.

17. The wallet of claim 16, wherein said folding changing pad separates said compartment from said pocket.

18. The wallet of claim 1, wherein said changing pad includes a magnet for temporarily attaching said changing pad to a ferrous or ferric surface.

19. The wallet of claim 1, wherein said first and second portions enclose an interior space when at said closed configuration.

* * * * *